United States Patent [19]

Schramm

[11] 4,368,731

[45] Jan. 18, 1983

[54] PISTOL-TYPE SYRINGE

[76] Inventor: Heinrich W. Schramm, Schweriner Strasse 24, D-4803 Steinhagen, Fed. Rep. of Germany

[21] Appl. No.: 233,690

[22] Filed: Feb. 12, 1981

[30] Foreign Application Priority Data

Feb. 12, 1980 [DE] Fed. Rep. of Germany ... 8003633[U]
Sep. 8, 1980 [DE] Fed. Rep. of Germany ... 8023910[U]

[51] Int. Cl.$^3$ .............................................. A61M 5/00
[52] U.S. Cl. ................................ 128/215; 128/218 D
[58] Field of Search ........... 128/218 R, 218 A, 218 C, 128/218 D, 218 F, 215, 213, 234; 222/309, 327, 326, 391

[56] References Cited

U.S. PATENT DOCUMENTS

| | | | |
|---|---|---|---|
| 3,905,365 | 9/1975 | Colombo | 128/218 C |
| 4,067,334 | 1/1978 | Haller | 128/218 A |
| 4,090,639 | 5/1978 | Campbell et al. | 128/218 C X |
| 4,194,505 | 3/1980 | Schmitz | 128/218 D |

*Primary Examiner*—John D. Yasko
*Attorney, Agent, or Firm*—Schwartz, Jeffery, Schwaab, Mack, Blumenthal & Koch

[57] ABSTRACT

Disclosed is a pistol-type syringe for injecting the contents of an ampoule or the like by means of an axial displaceable piston. The syringe includes a handle member with a generally flat frontal surface having a bore through which an axially displaceable plunger member is positioned. The ampoule or the like is held in a position coaxial with the plunger. The plunger is provided with a generally disk-shaped pressure piece which is slidable along the plunger and which has a rest position defined by the flat frontal surface of the handle member. The handle member also has an associated activating lever which is operable to exert a force on the pressure piece.

13 Claims, 5 Drawing Figures

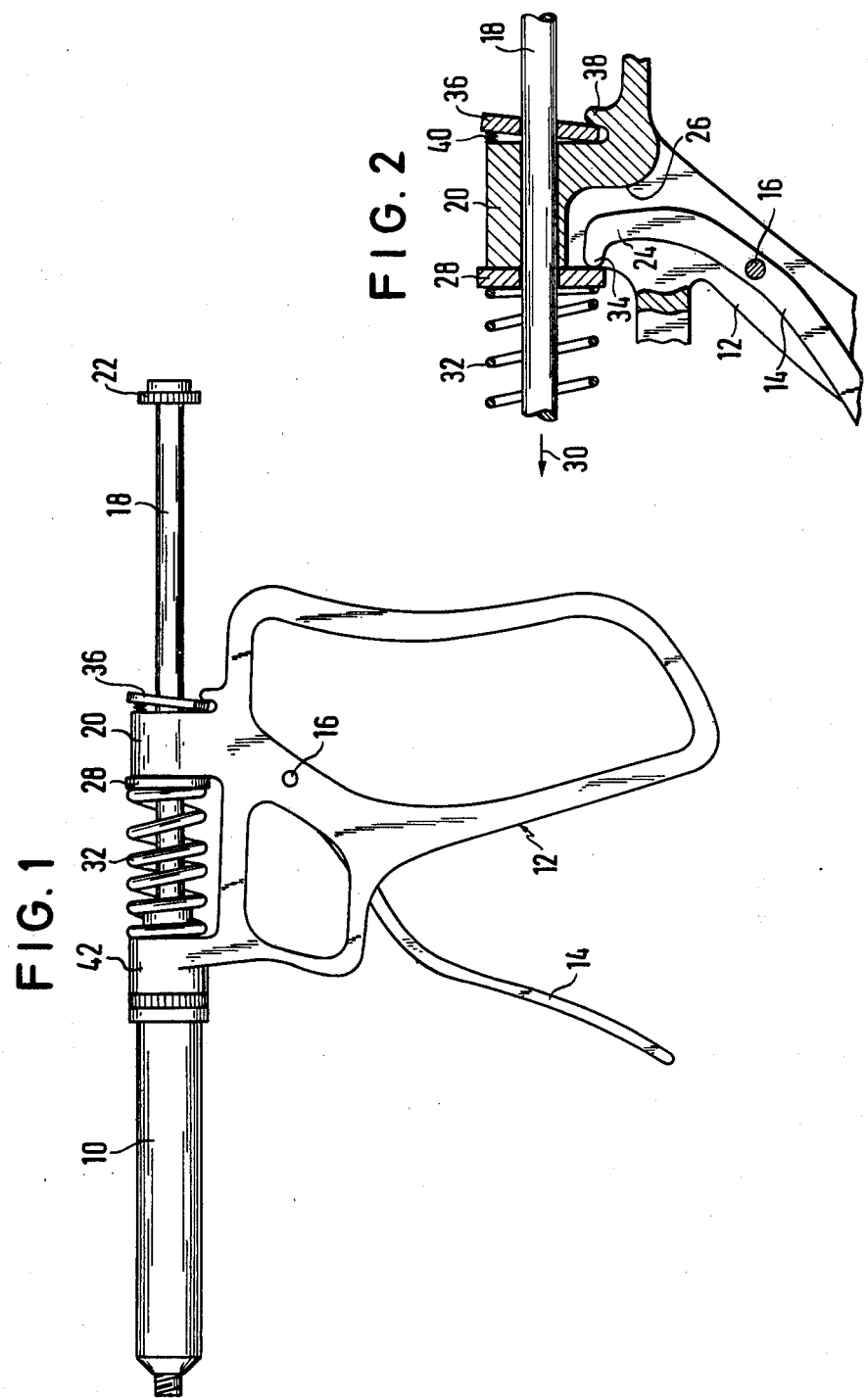

PISTOL-TYPE SYRINGE

BACKGROUND OF THE INVENTION

The invention pertains to a pistol-type syringe having a cylindrical holder for a cylindrical ampoule, a handle with a pivotable actuating lever and a pressure plunger connected with the actuating lever and guided coaxially in the holder, for the displacement of a piston contained in the cylindrical ampoule.

Pistol-type syringes of this type are known in various embodiments. To illustrate the state of the art, reference is made to German Offenlegungsschrift No. 23 58 838, corresponding to U.S. Pat. No. 3,905,365.

In syringes of this type, certain technical difficulties are caused by the transmission of force between the actuating lever and the pressure plunger, since this force transmission operates not only in the manner of a one-way clutch, but must also make possible a transition between the pivoting motion of the actuating lever and the linear movement of the plunger. In the known solutions to this problem, in most cases a tooth arrangement or grooving is provided on the plunger, which is engaged primarily by a movable connecting element fastened to the actuating lever. Such a tooth arrangement or grooving renders impossible an absolutely continuous (i.e., without steps) action by the driving force applied by the actuating lever at any arbitrary point of the plunger.

Furthermore, pistol-type syringes of the above-described type require a braking device to prevent the return of the pressure plunger upon the release of the actuating lever, as a result of the internal pressure of the cylindrical ampoule. Heretofore, mostly simple friction brakes have been used, the braking action of which naturally decreases to a significant degree with progressive wear.

It is desirable to be able to observe the process taking place within the cylindrical ampoule, i.e., in particular the movement of the piston within the cylindrical ampoule, from the outside through a window of the holder. On the other hand, cylindrical ampoules which consist of relatively thin glass or a synthetic material burst with relative ease, when excessive pressure is applied to them by means of the actuating lever, so that the injection solution contained in the ampoule escapes through the window, together with fragments of the ampoule.

SUMMARY OF THE INVENTION

The problem underlying the invention is to provide a pistol-type syringe of the above-mentioned type which contains a reliable drive connection between the actuating lever and the pressure plunger, in particular a drive connection which operates with little wear, with an absolutely continuous action and which can be operated with considerable sensitivity.

Furthermore, a braking device is to be provided which will hold the plunger reliably against rearwardly directed forces.

The problem underlying the invention is solved by a pistol-type syringe of the above-described type in that the pressure plunger, a longitudinally displaceable, disk-shaped pressure piece, surrounding the plunger with a slight spacing, is provided and in that the end of the actuating lever facing the plunger may be pressed essentially parallel to the advance direction of the plunger, and at a radial distance from the plunger, against the pressure piece.

As the disk-shaped pressure piece is guided on the pressure plunger with a relatively slight spacing or play, it will cant under a compressive stress applied parallel to the axis of the plunger but excentrically to it, so that the plunger will be carried by the actuating lever by means of the tightly jammed pressure piece.

The pressure plunger may have a smooth surface, so that it may not only be made of simple rod material and requires no additional surface structure, but it may also be seized by the pressure piece entirely continuously (without steps) in any position desired.

The pressure piece may be designed as a plate-like disk with a central aperture and may slide on a cylindrical pressure plunger. Preferably, a return spring is provided, which biases the pressure piece constantly toward the rear against the actuating lever and returns it upon the retraction of said actuating lever.

Designations, such as "rearward" and "forward" refer in the present context to the working direction of the syringe.

To form a brake device, a corresponding, additional disk-shaped pressure piece is provided, which again surrounds the plunger with a slight spacing or play. A stop is placed in the radially outer area of the second pressure piece, to the rear of it on the syringe, in particular on the handle. Should the last-mentioned pressure piece be carried along during the return motion of the plunger, its peripheral area will be arrested by the stop, so that the pressure piece will tilt on the plunger and become tightly jammed. This jamming action may be assisted by a suitable spring biasing the pressure piece into its canted position.

Within the holder, a preferably transparent intermediate tube may be provided, surrounding the cylindrical ampoule. This transparent intermediate tube makes it possible to observe the process taking place inside the cylindrical ampoule, while preventing the escape of the injection solution, should the cylindrical ampoule be destroyed.

BRIEF DESCRIPTION OF THE DRAWINGS

In the following portion, preferred embodiments of the invention will be explained in more detail with the aid of the drawings attached hereto.

FIG. 1 is a lateral elevation view of a pistol-type syringe according to the invention;

FIG. 2 is a partial sectional detail representation illustrating the pressure pieces and the manual handle and head piece;

DETAILED DESCRIPTION OF PREFERRED EMBODIMENTS

Figure 3:
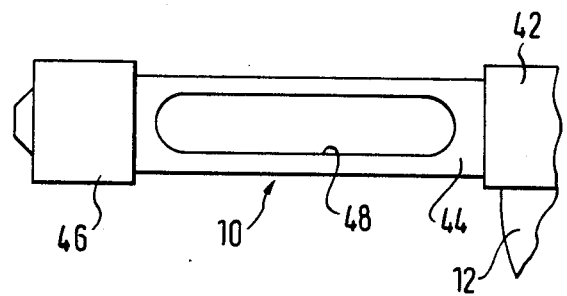
FIG. 3 is a partial side elevation view of one embodiment of the ampoule holder.

In FIG. 1, on the left hand side an essentially tubular holder 10 is shown, into which a conventional cylindrical ampoule for injection liquids (not shown) may be inserted. To insert the cylindrical ampoule, for example, a cap (not illustrated in detail) may be screwed off the front end of the holder, or the holder may alternatively be releasable altogether with respect to the remaining part of the syringe, so that the cylindrical ampoule may be inserted from the rear.

From the holder 10, a handle 12 extends essentially in a vertical direction, whereby the syringe may be gripped in the manner of a pistol. In the handle 12, a pivotable actuating lever 14 is integrated in a suitable manner, being mounted on bearings on an axle 16 in the handle. The actuating lever 14 may be gripped and retracted with the fingers of one hand. In this manner, as shall be explained in more detail hereinafter, a piston (not illustrated) is pressed from the rear into the cylindrical ampoule, so that the injection liquid will exit forward through a needle (not illustrated), i.e., to the left in FIG. 1. The ampoule is not shown in FIG. 1, but is illustrated in detail in FIG. 4.

The actuating lever 14 acts with its upper end on a pressure plunger 18, which is urged by the actuating motion toward the left in FIG. 1, i.e., into the holder 10 and therein impacts the piston directly. The plunger 18 is guided not only in the holder 10, but additionally in an upper head piece 20 of the handle 12, in a longitudinally displaceable manner. A head 22 is found at the rear end of the plunger 18, with the help of which the plunger 18 may be retracted, when necessary.

The transmission of force between the actuating lever 14 and the plunger 18 shall be explained in detail hereinafter, the simultaneous reference to FIGS. 1 and 2.

The upper end 24 of the actuating lever 14 projects forward from a slit 26 inside the head piece 20, upon pulling of the actuating lever 14, i.e., to the left in FIGS. 1 and 2. During this projecting movement, the upper end 24 of the actuating lever 14 acts upon the lower rim of pressure piece 28 designed in the form of a disk. The pressure piece is guided on the pressure plunger 18 in a longitudinally displaceable manner and with a slight tolerance or play. As the result of this excentric application of pressure, the pressure piece 28 is tilting on the plunger 18, so that it will be jammed against the plunger 18, thus carrying along the plunger in the direction of the arrow 30.

Between the pressure piece 28 and the rear end of the holder 10, there is a helical compression spring 32 which surrounds the pressure plunger 18 within this area. Upon release of the actuating lever 14, the helical compression spring 32 returns the pressure piece 28 against the undesignated left frontal side of the head piece 20, serving as a butt surface. In this manner, the helical compression spring simultaneously serves as the return spring for the actuating lever.

Since the transmission of force between the actuating lever 14 and the plunger 18 is effected by the canting and resultant jamming of the pressure piece 28, it is not necessary to form grooves, teeth or the like on the plunger 18.

The adaptation of the pivoting motion of the actuating lever 14 to the purely axial motion of the pressure plunger 18 and thus of the pressure piece 28 takes place in such a way that the upper end 24 of the actuating lever 14 is directed slightly outwardly in the radial direction of the pressure piece 28 during the advance movement. In order to prevent wear, the upper end 24 may be provided with a spherically rounded, forwardly directed head 34. Since the pressure piece 28 may be rotated on the plunger 18, any wear of the surface of the pressure piece 28 is distributed over its entire circumference.

A further pressure piece 36 is provided on the rear side of the head piece 20, which may have the configuration similar to that of the pressure piece 28, that is, of a circular disk, sliding with a slight tolerance on the plunger 18. This additional pressure piece 36 abuts against the rear frontal surface of the head piece 20 and is secured at its lower edge against displacement in the rearward direction by a stop 38 extending from the head piece or the handle. Whenever the plunger 18 is tending to perform a rearward motion, the pressure piece 36 will be arrested at its lower edge by the stop 38, so that it will be canted on the plunger 18, thereby immobilizing the plunger. The pressure piece 36 thus serves as a braking device. To assist this canting motion and to limit the dead run prior to the onset of the braking effect, the pressure piece 36 may be biased in the area of the upper edge of the head piece 20, for example, by means of a compression spring 40. When the braking action is to be released and the plunger 18 retracted, it is merely necessary to press the pressure piece 36 with its entire surface against the rear frontal surface of the head piece 20.

It has already been pointed out that it is not necessary to design the plunger 18 in the form of a cylindrical rod and the pressure pieces 28, 36 as circular disks. Other cross-sectional shapes for these pieces can be employed. The use of such parts does, however, offer the advantage that the force transmission and braking mechanism may be made of commercially available parts, requiring little processing.

Figure 4:
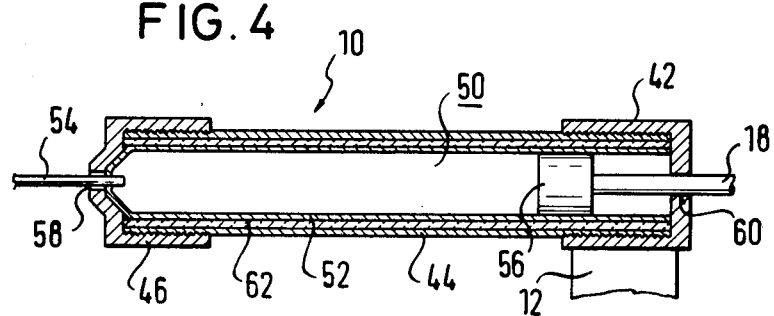
FIG. 4 is a longitudinal section of FIG. 3.

FIGS. 3 and 4 show details of an embodiment of the cylindrical holder 10, indicated in a simplified representation in the left hand part of FIG. 1. A receiving part 42 is located at the upper end of the handle 12, with a sleeve 14 being screwed into said piece 42. A cap 46 is screwed onto the front end of the sleeve 44. The sleeve 44 has a plurality of elongated windows 48 making it possible to observe the process taking place inside the holder during the expulsion of the content of a cylindrical ampoule.

According to FIG. 4, a cylindrical ampoule 50 is located inside the holder 10. The cylindrical ampoule 50 consists of a cylinder 52, mostly made of glass, with an injection needle 54 being insertable into the front end of said cylinder and a piston 56 being slidingly displaceable therein. By the displacement of the piston 56 from the right to the left in FIG. 4, the injection solution is ejected from the cylinder 52 through the injection needle 54, in a manner well known. The cap 46 has a passage 58 for the injection needle 54 and supports the cylinder 52 from the left side in FIG. 4.

The piston 56 is displaced by the plunger 18 according to FIGS. 1 and 2, with the plunger being displaceable in a center bore 60 of the receiving piece 42.

With the aid of the actuating lever 14 and the pressure plunger 18, a considerable force may be applied to the piston 56, which could lead to the destruction of the cylindrical ampoule if the piston 56 cannot be moved uniformly within the cylinder 52. Should the cylindrical ampoule 50 burst, the injection solution would escape through the windows 48 of the holder, together with any fragments of the ampoule. In order to prevent this from happening, an intermediate tube 62 is located within the sleeve 44 of the holder 10, which occupies the entire length of the holder and is secured therein by the cap 46, but is otherwise loosely displaceable and rotatable within the sleeve 44. This intermediate tube may consist of a transparent material, such as an acrylic glass, so that the process taking place within the holder may be observed through the windows 48. After the cap 46 has been removed, the intermediate tube may be gripped with two fingers through the windows 48 and pushed out in the forward direction. In case of the destruction of a cylindrical ampoule, the ampoule together with its content is retained initially in the holder and may be taken out with the intermediate tube.

Figure 5:
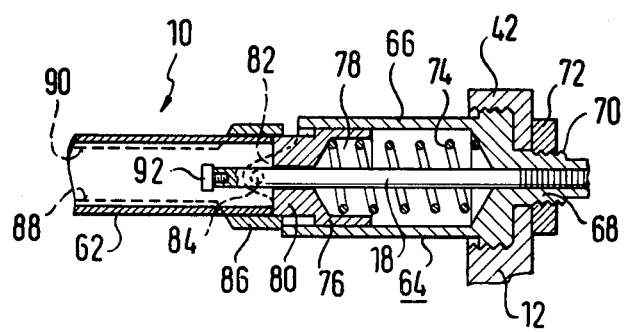
FIG. 5 is a side view, partially in section, illustrating another embodiment of the invention, pertaining to the connection between the holder and the handle.

FIG. 5 shall now be discussed. The embodiment according to FIG. 5 differs from that of FIGS. 3 and 4, in particular, by a different connection between the holder 10 and the handle 12.

A receiving piece essentially corresponding to the receiving piece 42 is again provided at the upper end of the handle 12, and therefore carries the same reference numeral 42. The receiving piece 42 has internal threads and a center bore corresponding to the center bore 60 of FIG. 4. A guide piece 64 is screwed into the inner threads. It penetrates the center bore of the receiving piece 42 and broadens out in the form of a hollow cylinder in the section 66, to the left of the receiving piece 42 in FIG. 5. A right hand section 68 of the guide piece 64 has external threads 70 and surrounds the plunger 18 in the shape of a tube. A nut 72 is screwed onto the external threads to the right of the receiving piece 42; it additionally secures the guide piece 64 with respect to the handle 12.

The pressure plunger 18 enters the hollow cylindrical section 66 of the guide piece 64 and is surrounded therein by a helical compression spring 74, supported at the right in FIG. 5 by the conical bottom of the hollow cylindrical section 66. Displaceably slideable in the section 66 is a rotationally symmetrical pressure piece 76 which has a recess 78 with a conical bottom facing the helical compression spring 74. The left end of the helical compression spring 74 is supported on the conical bottom of this recess. The pressure piece 76 further has a center bore as an extension of the center bore of the tubular section 68, which guides the plunger 18. The pressure piece 76, having an external diameter essentially corresponding to the inner diameter of the hollow cylindrical section 66 of the guide piece 64, has at its left hand end in FIG. 3 a section 80 with a reduced diameter, which shall be discussed hereinbelow.

At the left hand end of the hollow cylindrical section 66 of the guide piece 64, there are located two ears 82, indicated in opposing positions by broken lines, said ears holding two pins 84 aligned with each other, with a sleeve designated by 86 being pivotably supported thereon. The axis of rotation of the sleeve 86 is perpendicular to the plane of the drawing in FIG. 5. This sleeve 86 corresponds to the sleeve 44 according to FIGS. 3 and 4. The sleeve 86 is closed off in a manner not shown, at its left end, but it is possible to take out the intermediate tube 62 by tilting the sleeve 86 down approximately at right angles around the pins 84 with respect to the guide piece 64. The sleeve 86 has windows 88, 90 on opposing sides, similar to windows 48 in sleeve 44 illustrated in FIG. 3.

As seen in FIG. 5, the pressure piece 76 has in its left hand section 80 an external diameter corresponding to the inner diameter of the sleeve 86, so that the pressure piece may enter said sleeve. This entry, which is automatic under the effect of the helical compression spring 74, on the one hand, serves to press the intermediate tube 61 against the left end of the sleeve 86 (not shown) and on the other hand, serves to arrest the sleeve 86 in the operating position indicated in FIG. 5.

The pressure plunger 18 carries at its left end a screwed-in head piece 92, having a cross-sectional area slightly larger than the plunger 18 and together with the pressure piece 76, forming a stop during the withdrawal of the plunger 18 toward the right in the drawing. On the other hand, the head piece 92 makes it possible to withdraw the pressure piece 76 from the sleeve 86 against the action of the helical compression spring 74 by means of a handle, (not shown), provided at the right end of the plunger, and thus to release the locking of the sleeve, so that the sleeve may be tilted down with respect to the guide piece 64. After tilting down, the intermediate tube 62 may be extracted at the rear side of the sleeve 86. It is therefore, for example, not necessary to provide a releasable cap 46, as in FIG. 4, at the left end of the sleeve 86 (which is not shown in FIG. 5).

I claim:

1. A pistol-type syringe for injecting the contents of an ampoule having therein a piston which discharges the contents upon axial displacement, said syringe comprising:

a handle member having an upper portion with a first generally flat frontal surface and having an axial bore extending therethrough;

an elongated plunger member longitudinally displaceably positioned in the bore;

means, associated with the upper portion of said handle member, for holding an ampoule in a position forward of said handle member and substantially coaxial with said plunger;

a generally disk-shaped first pressure piece having an aperture therein which is slightly larger than the outer circumference of said plunger member, said first pressure piece being slidably positioned on said plunger member and having a rest position defined by said first surface of said upper portion of said handle member, said rest position being generally perpendicular to the axis of said bore; and an actuating lever pivotably mounted on said handle, the upper end of said lever being adapted upon pivoting of said lever to exert a force on said pressure piece in a direction generally parallel to said plunger member and at a position on said first pressure piece spaced radially outwardly from said plunger member.

2. A syringe according to claim 1, wherein said ampoule holding means comprises a tubular guide piece connected to said handle member, said guide piece having radially opposing longitudinal extensions extending in the forward direction, a generally tubular ampoule holder pivotably mounted on said extension for rotation into and out of coaxial alignment with said guide piece, a third pressure piece having an aperture therein larger than the circumference of said plunger member, said third pressure piece being slidably positioned inside of said guide piece and having a front portion which has an outer dimension equal to the inner dimension of said ampoule holder, means for normally spring biasing said third pressure piece forwardly so that said front portion extends into said ampoule holder, and means for selectively withdrawing said front portion from said ampoule holder so that said ampoule holder can be rotated for insertion and removal of an ampoule from the rear.

3. A pistol type-syringe for injecting the contents of an ampoule having therein a piston which discharges the contents upon axial displacement, said syringe comprising:

a handle member having at its upper portion a bore extending therethrough;

an elongated plunger member longitudinally displaceably positioned in the bore;

ampoule holding means, associated with the upper portion of said handle member for holding an ampoule in a position forward of said handle member and substantially coaxial with said plunger;

said ampoule holding means comprising a tubular guide piece connected to said handle member, said guide piece having radially opposing longitudinal extensions extending in the forward direction, a generally tubular ampoule holder pivotably mounted on said extension for rotation into and out of coaxial alignment with said guide piece, a third pressure piece having an aperture therein larger than the circumference of said plunger member, said third pressure piece being slidably positioned inside of said guide piece and having a front portion which has an outer dimension equal to the inner dimension of said ampoule holder, means for normally spring biasing said third pressure piece forwardly so that said front portion extends into said ampoule holder, and means for selectively withdrawing said front portion from said ampoule holder so that said ampoule holder can be rotated for insertion and removal of an ampoule from the rear;

a generally disk-shaped first pressure piece having an aperture therein which is slightly larger than the outer circumference of said plunger member, said first pressure piece being slideably positioned on said plunger member; and an actuating lever pivotingly mounted on said handle, the upper end of said lever being adapted upon pivoting of said lever to exert a force on said pressure piece in a direction generally parallel to said plunger member and at a position on said first pressure piece spaced radially outwardly from said plunger member.

4. A syringe according to claim 1 or 3, wherein said plunger member comprises a generally cylindrical, smooth rod and wherein said pressure piece comprises a circular disk with a center bore.

5. A syringe according to claim 1 or 3, further comprising a spring for biasing said pressure piece against said handle member.

6. A syringe according to claim 1 or 3, wherein said upper portion of said handle member includes a head piece containing the bore, said head piece having said first frontal surface and a slit on its side facing said handle member, wherein the upper end of said actuating lever projects forward from the slit in the head piece, wherein said pressure piece is arranged in front of the forward frontal surface of said head piece and wherein said spring comprises a helical compression spring positioned between said pressure piece and the rear end of said ampoule holding means, said spring surrounding said plunger member.

7. A syringe according to claim 6, wherein the upper end of said actuating lever comprises a spherically rounded head pointing in the forward direction for engaging with said pressure piece.

8. A syringe according to claim 6, further comprising means for braking rearward motion of said plunger member.

9. A syringe according to claim 6, wherein said braking means comprises a second generally disk-shaped pressure piece having an aperture therein which is slightly larger than the outer circumference of said plunger member, said second pressure piece being slidably positioned on said plunger member, and stop means positioned on said handle member for engaging the peripheral area of said second pressure piece and stopping rearward movement thereof.

10. A syringe according to claim 9, wherein said handle member includes a second generally flat surface facing to the rear opposite to said first frontal surface and being generally perpendicular to the axis of said bore and wherein said second pressure piece is located proximate to said second surface of said head piece and wherein said stop means projects upwardly from said handle member.

11. A syringe according to claim 9, wherein said braking means further comprises means for biasing said second pressure piece in the rearward direction at its periphery radially opposite said stop means.

12. A syringe according to claim 1 or 3, wherein said ampoule holding means includes at least one window, and further comprising a transparent intermediate tube member positioned in said ampoule holding means.

13. A syringe according to claim 1 or 3, wherein said withdrawing means comprises an enlarged forward end portion on said plunger member having an outer dimension larger than the aperture in said third pressure piece and a grasping portion at the opposite end of said plunger member.

* * * * *